United States Patent [19]

Adelstein

[11] 4,028,364
[45] June 7, 1977

[54] 2-AZABICYCLO[2.2.2.]OCTAN-2-YL-DIPHENYL-ALKANONES AND RELATED COMPOUNDS

[75] Inventor: Gilbert William Adelstein, Evanston, Ill.

[73] Assignee: G. D. Searle & Co., Chicago, Ill.

[22] Filed: July 6, 1976

[21] Appl. No.: 703,041

[52] U.S. Cl. .......................... 260/293.54; 424/267
[51] Int. Cl.² ...................................... C07D 453/02
[58] Field of Search ............................... 260/293.54

[56] References Cited

UNITED STATES PATENTS

| 3,318,869 | 5/1967 | Cusic et al. | 260/239 |
| 3,917,615 | 11/1975 | Adelstein | 260/293.54 |

*Primary Examiner*—G. Thomas Todd
*Attorney, Agent, or Firm*—Joy A. Serauskas

[57] ABSTRACT

This invention encompasses novel 2-azabicyclo[2.2.2]-octan-2-yl-diphenyl-alkanones and related compounds. These compounds are useful as anti-diarrheal agents.

2 Claims, No Drawings

2-AZABICYCLO[2.2.2.]OCTAN-2-YL-DIPHENYL-ALKANONES AND RELATED COMPOUNDS

The present invention is concerned with 2-azabicyclo[2.2.2]octan-2-yl-diphenyl-alkanones and related compounds thereof. More particularly, this invention is concerned with compounds of the general formula

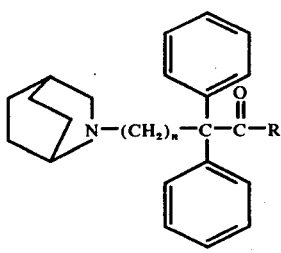

(I)

wherein R is an alkyl radical containing from 1 to 6 carbon atoms and n is an integer from 1 to 3.

The alkyl radicals are exemplified by methyl, ethyl, propyl, butyl, pentyl, hexyl and the corresponding branched chain isomers thereof.

A particularly preferred embodiment of this invention is that of formula (I) wherein R is ethyl and n is 2.

Equivalent to the compounds of formula (I) for the purposes of the invention are the pharmaceutically acceptable acid addition salts thereof. Such acid addition salts can be derived from a variety of inorganic and organic acids such as sulfuric, phosphoric, hydrochloric, hydrobromic, hydroiodic, sulfamic, citric, lactic, pyruvic, oxalic, maleic, succinic, tartaric, cinnamic, acetic, benzoic, salicylic, gluconic, ascorbic and related acids.

Compounds of the present invention are prepared as set out in the following scheme A.

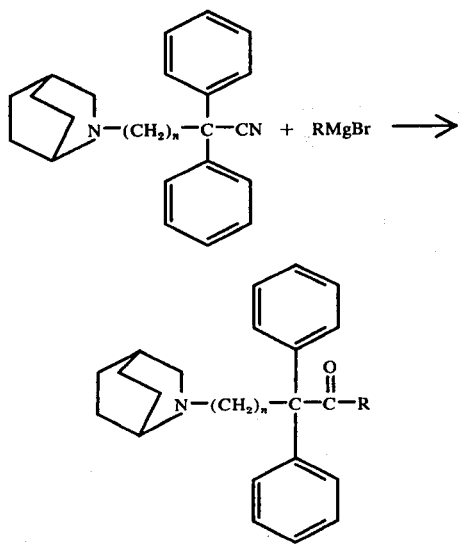

SCHEME A wherein R and n are defined as before.

Methods for preparing the nitrile precursors are described in U.S. Pat. No. 3,299,044 and include the reaction of diphenylacetonitrile of the formula

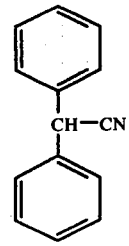

first with sodamide and then with an alkyl halide of the formula

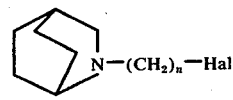

wherein Hal is chlorine or bromine and n is an integer from 1 to 3.

Alternately the nitriles can be prepared by the reaction of an appropriate amine with a halide of the formula

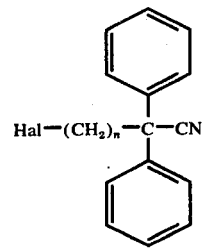

wherein Hal and n are defined as before.

As is illustrated by scheme A, the nitrile precursors are reacted with appropriate grignard reagents following the procedure which is substantially described by D. J. Dupre et al., Journal of Chemical Society p. 500–510 (1949) to give the compounds of the present invention.

For instance, 15.3 parts of ethyl magnesium bromide in ether is reacted with 7.5 parts of 2,2-diphenyl-4-(2-azabicyclo[2.2.2]octan-2-yl)butanenitrile in 20 parts by volume of dry toluene. After the reaction period is completed, the ether is removed leaving a solid material which is suspended in toluene. This mixture is then heated, cooled and left to stand overnight. 5% HCl is now added to the mixture and then the mixture is heated. After cooling the aqueous phase is extracted with toluene and these toluene washings are combined with the initial organic phase; this organic phase is now washed with 5% HCl. The initial aqueous phase and the HCl washings are combined and basified with 20% potassium hydroxide. This basic reaction mixture is now extracted with ether. The ether solution is filtered, dried, and reduced in vacuum to give a yellowish oil which crystallizes to provide 3-hexanone,6-(2-azabicyclo[2.2.2]octan-2-yl)-4,4-diphenyl.

The compounds of the present invention are useful in consequence of their valuable pharmacological properties. They are for example, anti-diarrheal agents as evidenced by their ability to inhibit gastrointestinal motility as set out in the following tests.

CHARCOAL MEAL TEST

The method used for this assay is a modification of the techniques previously described by Macht and Barba-Gose, *J. Amer. Pharm. Ass.*, 20, 558 (1931), and Janssen and Jageneau, *J. Pharm. Pharmacol.*, 9, 381 (1957). Details are as follows:

A group of six, male Charles River mice weighing 20-25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

CASTOR OIL-INDUCED DIARRHEA IN THE RAT

Adult Charles River male rats are fastened in community cages for 24 hours prior to the test, with free access to water. The test compound is then administered intragastrically (suspended on 0.5% methyl cellulose) one hour prior to the intragastric administration of a dose of 1.0 ml. castor oil per rat. The rats are then observed for the presence or absence of diarrhea at hourly intervals for up to 8 hours past the castor oil administration. Using the method of Berkson (1953), the median effective dose ($ED_{50}$) values are calculated at each hourly interval for the test compound.

A representative compound of this invention which is active in the Charcoal Meal Test anti-diarrheal assay and the Castor Oil-Induced Diarrhea in the Rat antidiarrheal assay is 3-hexanone, 6-(2-azabicyclo[2.2.2]octan-2-yl)-4,4-diphenyl. This representative compound has a median effective dose ($ED_{50}$) of 3.9 ± 0.9 mg./kg. IG in the Charcoal Meal Test and ($ED_{50}$) of 1.32 ± .24 mpk IG in the Castor Oil-Induced Diarrhea Test. Antidiarrheal agent, diphenoxylate, described in Goodman and Gilman's *The Pharmaceutical Basis of Therapeutics*, Collier Macmillan Linden (1970) page 258, is active in this test.

The compounds of formula (I) may be combined with various pharmaceutical carriers to provide compositions suitable for use in the treatment of diarrhea. The dosage of these compounds is dependent upon various factors, such as the compound employed and the particular response obtained. Typical dosages for use as an anti-diarrheal agent vary from 0.1 to 25 mg./kg. per day administered orally.

The following examples describe in detail the preparation of compounds of the present invention. It will be apparent to those skilled in the art that many modifications both of materials and method, may be practiced without departing from the purpose and intent of this disclosure. Throughout the examples hereinafter set forth, temperatures are given in degrees Centigrade (°C.) and relative amounts in parts by weight, except as otherwise noted.

EXAMPLE 1

15.3 Parts of ethyl magnesium bromide in ether is added dropwise with stirring to a solution of 7.5 parts of 2,2-diphenyl-4-[2-azabicyclo(2.2.2)octan-2-yl)]butanenitrile in 20 parts by volume of dry toluene. After the addition of the grignard reagent is completed, the ether is distilled off. Removal of the ether precipitated a solid material which is suspended in the toluene. This reaction mixture is then heated on a water bath for 6 hours, cooled and left to stand overnight. 5% HCl is now slowly added to this mixture. After the addition of the acid is completed, the reaction mixture is heated on a water bath for an hour. The reaction mixture is then separated into its organic and aqueous phase. The aqueous phase is now washed with additional toluene; these toluene washings are then combined with the initial organic phase and the organic phase is now washed with 5% HCl. The initial aqueous phase, the HCl washings, and an undissolved oil are combined and basified with 20% KOH. This reaction mixture is then extracted with ether; the ether extracts are then filtered, dried over magnesium sulfate and reduced in vacuum to give a yellowish oil which crystallizes upon standing. Recrystallization of this material from acetone and ether gives crystilline 3-hexanone, 6-[2-azabicyclo(2.2.2)-octan-2-yl]-4,4-diphenyl which melts at 181°-186° C. and has the following formula.

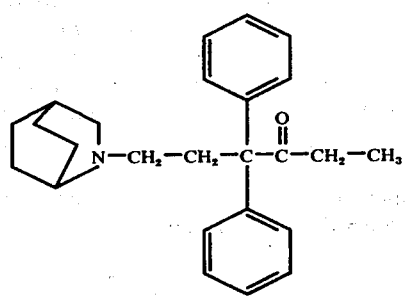

EXAMPLE 2

Substitution of n-hexyl magnesium bromide for the ethyl magnesium bromide of Example 1 and repetition thereof of the procedure which is described in Example 1 affords 4-decanone, 1-[2-azabicyclo(2.2.2)octan-2-yl]-3,3-diphenyl. This compound is represented by the following formula.

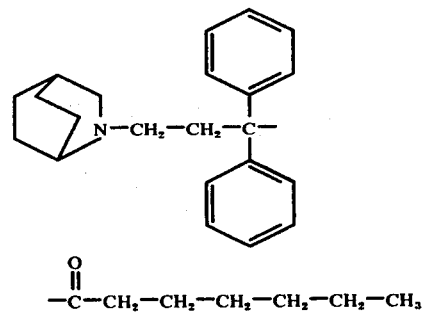

EXAMPLE 3

Repetition of the procedure detailed in Example 1 using an equivalent quantity of 2,2-diphenyl-6-[2- azabicyclo-(2.2.2)octan-2-yl]hexanenitrile in place of the 2,2-diphenyl-4-[2-azabicyclo(2.2.2)octan-2-yl]butanenitrile affords 3-octanone, 8-[2-azabicyclo(2.2.2)octan-2-yl]-4,4-diphenyl. This compound is represented by the following formula.

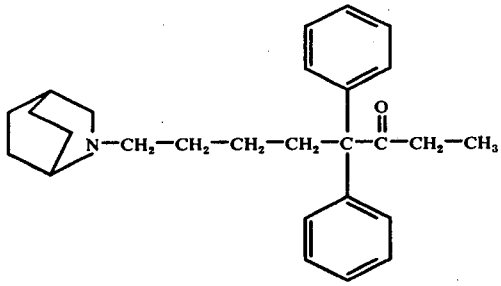

What I claim is:
1. A compound of the general formula

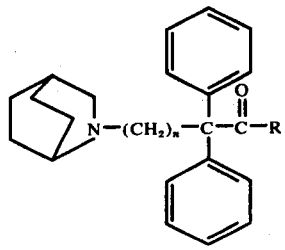

(I)

wherein R is an alkyl radical containing from 1 to 6 carbon atoms and $n$ is an integer from 1 to 3.

2. A compound according to claim 1 which is 3-hexanone,6-(2-azabicyclo[2.2.2]octan-2-yl)-4,4-diphenyl.

* * * * *